(12) United States Patent
Paranjape et al.

(10) Patent No.: US 9,302,908 B2
(45) Date of Patent: Apr. 5, 2016

(54) SYSTEMS AND PROCESS FOR FORMING CARBON NANOTUBE SENSORS

(75) Inventors: Makarand Paranjape, Silver Spring, MD (US); Jianyun Zhou, Los Angeles, CA (US)

(73) Assignee: Georgetown University, Washington, DC (US)

( * ) Notice: Subject to any disclaimer, the term of this patent is extended or adjusted under 35 U.S.C. 154(b) by 827 days.

(21) Appl. No.: 12/970,997

(22) Filed: Dec. 17, 2010

(65) Prior Publication Data

US 2012/0153262 A1    Jun. 21, 2012

(51) Int. Cl.
| H01L 21/66 | (2006.01) |
| B82Y 15/00 | (2011.01) |
| B82Y 10/00 | (2011.01) |
| G01N 27/414 | (2006.01) |
| H01L 51/00 | (2006.01) |
| H01L 51/05 | (2006.01) |
| B82Y 40/00 | (2011.01) |

(52) U.S. Cl.
CPC .............. B82Y 15/00 (2013.01); B82Y 10/00 (2013.01); G01N 27/4145 (2013.01); H01L 51/0048 (2013.01); B82Y 40/00 (2013.01); H01L 51/0558 (2013.01)

(58) Field of Classification Search
USPC ................. 257/24, E51.04; 438/49
See application file for complete search history.

(56) References Cited

U.S. PATENT DOCUMENTS

| 6,887,202 B2 | 5/2005 | Currie et al. ................. 600/309 |
| 7,670,831 B2 | 3/2010 | Lee et al. ................... 435/283.1 |
| 8,110,079 B2* | 2/2012 | Gooding et al. ......... 204/403.01 |
| 2005/0126913 A1 | 6/2005 | Burke et al. ................... 204/547 |
| 2005/0265914 A1* | 12/2005 | Gu et al. ..................... 423/445 B |
| 2007/0114457 A1* | 5/2007 | Han et al. .................. 250/492.21 |
| 2008/0093211 A1* | 4/2008 | Ramanath et al. ....... 204/157.63 |
| 2009/0068241 A1 | 3/2009 | Britz et al. ................... 424/409 |
| 2009/0212279 A1 | 8/2009 | Liu et al. .......................... 257/30 |
| 2010/0088040 A1 | 4/2010 | Johnson, Jr. .................... 702/27 |

(Continued)

FOREIGN PATENT DOCUMENTS

WO    WO 2007/064355 A2    6/2007

OTHER PUBLICATIONS

Zhou, Jianyun, et al., "Novel In-Situ Decoration of Single-Walled Carbon Nanotube Transistors With Metal Nanoparticles," *Journal of Nanoscience and Nanotechnology*, vol. 10, pp. 1-5, 2010.

(Continued)

*Primary Examiner* — Timor Karimy
(74) *Attorney, Agent, or Firm* — Dawn-Marie Bey; Bey & Cotropia PLLC

(57) ABSTRACT

A process for forming a functionalized sensor for sensing a molecule of interest includes providing at least one single or multi-wall carbon nanotube having a first and a second electrode in contact therewith on a substrate; providing a third electrode including a decorating material on the substrate a predetermined distance from the at least one single or multi-wall carbon nanotube having a first and a second electrode in contact therewith, wherein the decorating material has a bonding affinity for a bioreceptors that react with the molecule of interest; and applying a voltage to the third electrode, causing the decorating material to form nanoparticles of the decorating material on the at least one single or multi-wall carbon nanotube.

15 Claims, 7 Drawing Sheets

(56) References Cited

U.S. PATENT DOCUMENTS

2010/0239794 A1*  9/2010  Andrews et al. ............ 428/32.72
2010/0285514 A1  11/2010  Claussen et al. ................ 435/25

OTHER PUBLICATIONS

International Search Report and Written Opinion for Application Serial No. PCT/US2010/060929, dated Feb. 24, 2011, 7 pp.

Xiang, Yangchuan, "Synthesis and Electrochemical Characterization of Uniformly-Dispersed high Loading Pt Nanoparticles on Sonochemically-Treated Carbon Nanotubes," *J. Phys. Chem. B*, 108, pp. 19255-19259, 2004.

Girishkumar, G., "Carbon Nanostructures in Portable Fuel Cells: Single-Walled Carbon Nanotube Electrodes for Methanol Oxidation and Oxygen Reduction," *J. Phys. Chem. B*, 108, pp. 19960-19966, 2004.

Yao, Zhen, "High-Field Electrical Transport in Single-Wall Carbon Nanotubes," *Physical Review Letters*, vol. 84, No. 13, pp. 2941-2944, Mar. 27, 2000.

Gruner, G., "Carbon Nanotube Transistors for Biosensing Applications," Department of Physics, University of California Los Angeles, and Nanomix, Inc.

Allen, Brett Lee, "Carbon Nanotube Field-Effect-Transistor-Based Biosensors," *Advanced Materials*, 19, pp. 1439-1451, 2007.

Balasubramanian, Kannan, "Biosensors Based on Carbon Nanotubes," *Anal Bioanal Chem.*, 385: 452-478, 2006.

Gruner, G., "Carbon Nanotube Transistors for Biosensing Applications," *Anal Bioanal Chem*, 384: 322-335, 2006.

Capek, Ignac, "Dispersions, Novel Nanomaterial Sensors and Nanoconjugates Based on Carbon Nanotubes," *Advances in Colloid and Interface Science*, 150, pp. 63-89, 2009.

Claussen, Jonathan C., et al., Electrochemical Biosensor of Nanocube-Augmented Carbon Nanotube Networks [online], *ACS Nano*, [Retrieved on Jan. 25, 2009, Retrieved from the Internet: http://pubs.acs.org, 9 pp.

Cella, Lakshmi N., et al., "Single-Walled Carbon Nanotube-Based Chemiresistive Affinity Biosensors for Small Molecules: Ultrasensitive Glucose Detection," *J. Am. Chem. Soc.*, JACS Communication, Jan. 19, 2010.

Day, Thomas M., et al., "Electrochemical Templating of Metal Nanoparticles and Nanowires on Single-Walled Carbon Nanotube Networks," *J. Am. Chem. Soc.*, 127, pp. 10639-10647, 2005.

Quinn, Bernadette M., "Electrodeposition of Noble Metal Nanoparticles on Carbon Nanotubes," *J. Am. Chem. Soc.*, 127, pp. 6146-6147, 2005.

D. R. Kauffman and A. Star, "Chemically Induced Potential Barriers at the Carbon Nanotube-Metal Nanoparticle Interface," *Nano Lett.*, vol. 7, No. 7, pp. 1863-1868, 2007.

A. Star, et al., "Label-Free Detection of DNA Hybridization Using Carbon Nanotube Network Field-Effect Transistors," *Proc. Natl. Acad. Sci. USA*, 103(4), pp. 921-926, Jan. 24, 2006.

T. Ozel, et al., "Polymer Electrolyte Gating of Carbon Nanotube Network Transistors," *Nano Lett*, vol. 5, No. 5, pp. 905-911, 2005.

K. J. Cash, et al., "Nanosensors and Nanomaterials for Monitoring Glucose in Diabetes," *Trends in Molecular Medicine*, vol. 16, Issue 12, pp. 584-593, Sep. 23, 2010.

J. Zhang, et al., "Mechanism of $NO_2$ Detection in Carbon Nanotube Field Effect Transistor Chemical Sensors," *Appl. Phys. Lett.*, 88(12), 3 pp., 2006.

J. Zhou, "Fabrication and Functionalization of Carbon Nanotube Field Effect Transistors for Bio-Sensing Applications," Graduate School of Arts and Sciences, Georgetown University, Dec. 17, 2009.

Chu, Haibin, et al., "Site-Specific Deposition of Gold Nanoparticles on SWNTs," J. Phys. Chem. C, 112, pp. 13437-13441, 2008.

Gao, Ruifang, et al., "Amine-Terminated Ionic Liquid Functionalized Carbon Nanotube-Gold Nanoparticles for Investigating the Direct Electron Transfer of Glucose Oxidase," Electrochemistry Communications 11, pp. 608-611 (2009).

Lee, Chung-Hun, et al., "Comparison of Amperometric Biosensors Fabricated by Palladium Sputtering, Palladium Electrodeposition and Nafion/Carbon Nanotube Casting on Screen-Printed Carbon Electrodes," Biosensors and Bioelectronics 22, pp. 877-884 (2007).

A. Star, J. Phys. Chem. B, 2006, 110, pp. 21014-21020.

\* cited by examiner

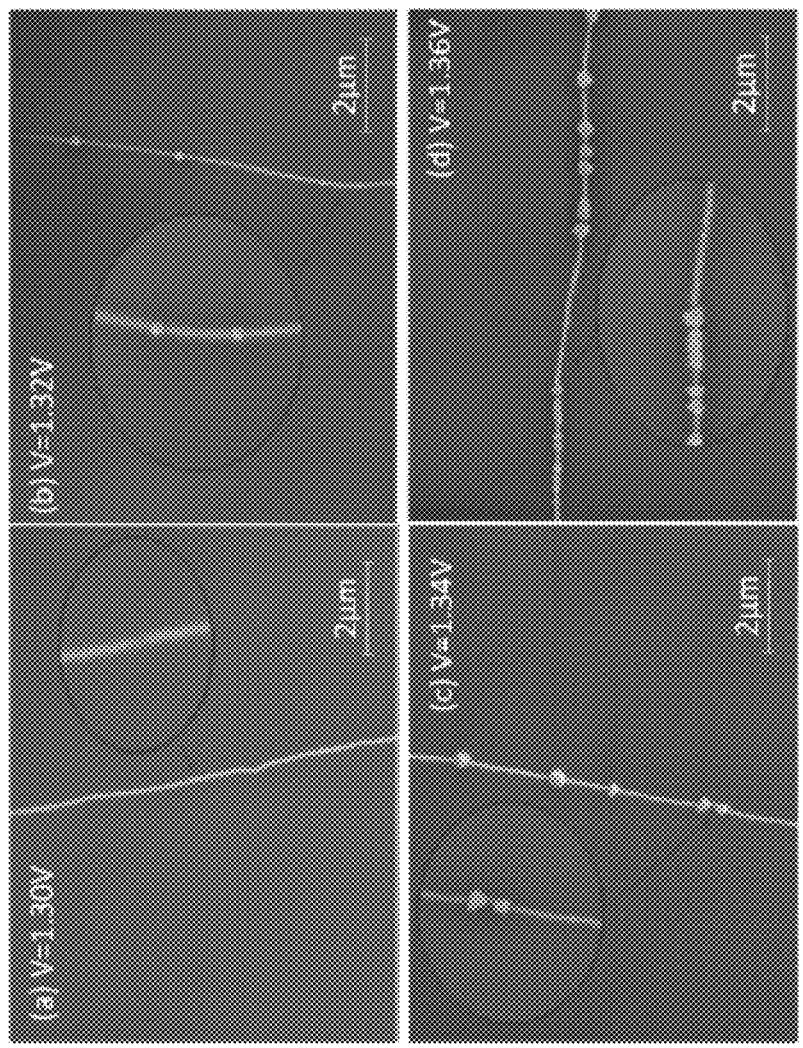
Figure 3(a)-(d)

SYSTEMS AND PROCESS FOR FORMING CARBON NANOTUBE SENSORS

BACKGROUND OF THE INVENTION

1. Field of the Invention

The present invention relates generally to the use of carbon nanotube technology in the field of sensor applications. More specifically, this invention relates to processes for forming and functionalizing of carbon nanotube field effect transistors ("CNTFETs") for use in specific sensor systems, such as chemical and biological sensors.

2. Description of the Related Art

Sensor technology has long been an active area of interest to numerous entities including the medical community, law enforcement, national defense and basic research. The ability to accurately detect and analyze the presence (or absence) of various molecules in central to many applications. By way of specific example, the medical community continues to seek non-invasive or minimally invasive ways to monitor patient health. Commonly owned U.S. Pat. No. 6,887,202 describes various approaches to transdermal monitoring. The teachings and descriptions of U.S. Pat. No. 6,887,202 are incorporated herein by reference in their entirety.

The present application describes an improved sensor configuration compatible with many of the configurations described in U.S. Pat. No. 6,887,202, wherein the improved sensor meets current demands for reduced size and improved sensing characteristics.

BRIEF SUMMARY OF THE INVENTION

A first embodiment includes a process for forming a functionalized sensor for sensing a molecule of interest. The process includes: providing at least one single-wall carbon nanotube having a first and a second electrode in contact therewith on a substrate; providing a third electrode including a decorating material on the substrate a predetermined distance from the at least one single-wall carbon nanotube having a first and a second electrode in contact therewith, wherein the decorating material has a bonding affinity for a bioreceptors that react with the molecule of interest; and applying a voltage to the third electrode, causing the decorating material to form nanoparticles of the decorating material on the at least one single-walled carbon nanotube.

A second embodiment describes a system for forming a functionalized sensor for sensing a molecule of interest including: at least one carbon nanotube having a first and a second electrode in contact therewith on a substrate; a third electrode including a decorating material on the substrate a predetermined distance from the at least one carbon nanotube having a first and a second electrode in contact therewith, wherein the decorating material has a bonding affinity for a bioreceptors that react with the molecule of interest; wherein a voltage is applied to the third electrode, causing the decorating material to form nanoparticles of the decorating material on the at least one carbon nanotube.

BRIEF DESCRIPTION OF THE FIGURES

FIGS. 3(a)-3(d) illustrate a series of SEM images showing deposition particulars at different voltages.

DETAILED DESCRIPTION OF THE PREFERRED EMBODIMENTS

In an embodiments described herein, carbon nanotube field effect transistors ("CNTFETs") may be decorated with nanoparticles as further described to facilitate the binding of chemical/biological molecules of interest thereto. CNTFETs generally includes one or more CNTs, one or more electrodes contacting the two ends of the nanotube(s), an insulating dielectric layer (e.g., $SiO_2$) on top of or underneath the nanotube(s), and a conductive gate (e.g., doped silicon (if underneath of the nanotube), or a metallic top-gate (if on top of the nanotube) within a few hundred nanometers to the nanotube but insulated by the dielectric layer. Various techniques are used to developed CNTs including discharge, laser ablation and chemical vapor deposition ("CVD") and such techniques are well known to those skilled in the art. The electrodes may be patterned using photolithography or electrode beam lithography. Further, the electrodes may be metallic or non-metallic (e.g., conductive polymers, indium-tin-oxide (ITO) and the like.

Figure 1:
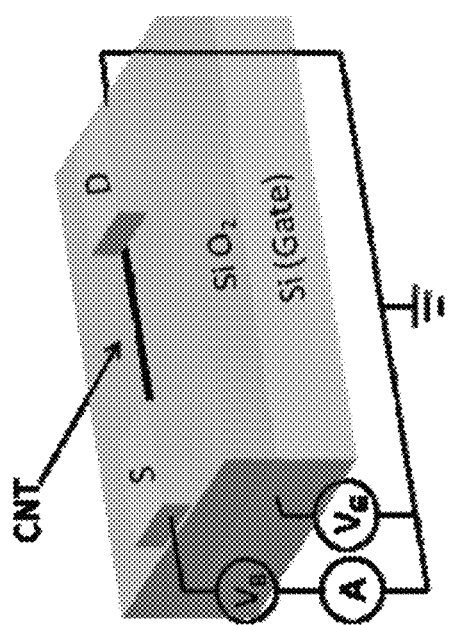
FIG. 1 illustrates a carbon nanotube field effect transistor (CNTFET) for use with embodiments of the present invention.

By way of specific example, a single wall CNT ("SWCNT") is used as the conduction channel in a CNTFET implemented as the sensor in the devices described herein. FIG. 1 shows a CNTFET including SWCNT, first and second electrodes (S=source; D=drain), insulating dielectric layer (e.g., $SiO_2$) and conductive gate (Si). One skilled in the art recognizes that CNTFETs may be formed using multiple CNTs, including CNT films or networks, including multiple CNTs, as described in the teachings of A. Star, E. Tu, J. Niemann, J.-C. P. Gabriel, C. S. Joiner, and C. Valcke, Proc Natl Acad Sci USA. 2006 Jan. 24; 103(4): 921-926 and T. Ozel, A. Gaur, J. A. Rogers, and M. Shim, *Nano Lett.*, 2005, 5 (5), pp 905-911 which are incorporated herein by reference. In order to prepare the SWCNT for use in particular sensing applications and integrated devices, a functionalization process is employed. Functionalizing the CNT requires not only successful attachment of molecules to the CNT, but also preservation of the CNT's intrinsic electronic properties. In addition, in a device environment, the specificity of the attachment becomes important since any unintended attachment will potentially introduce noise to the device. While the present embodiments contemplate a conductive substrate and thus a constraint on types of materials that may be used, embodiments are contemplated which utilize a top gate and thus the substrate is not constrained and can include glass, ceramic, plastic, etc. Further, while the specific embodiment described herein refers to at least one single wall CNT, the use of multi wall CNTs are also contemplated.

Figure 2A:
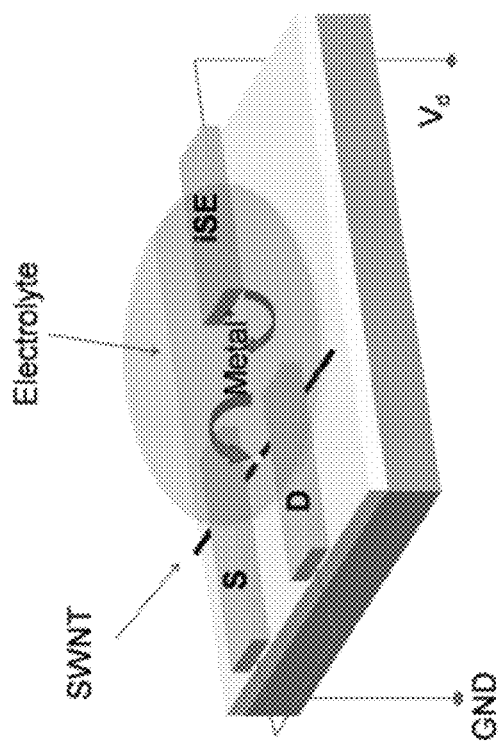
FIGS. 2(a)-2(b) illustrate representative and actual set-up configurations for functionalizing carbon nanotubes.
Figure 2B:
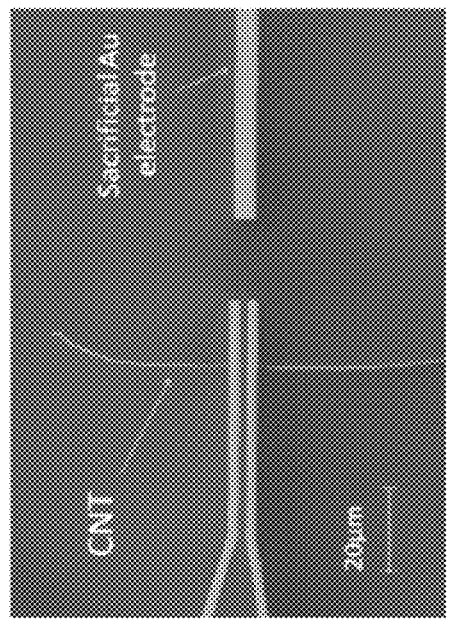

In a preferred embodiment, the SWCNT is functionalized using electrically controllable Au nanoparticle decoration. Referring to FIG. 2(a), the set up for facilitating Au decoration includes the addition of a third electrode in close proximity to, but not directly in contact with the SWCNT. Specifically, the third electrode serves as a source of Au and is sacrificed after the Au deposition. The third electrode may be referred to as the "in-situ sacrificial electrode" (iSE). In a particular example, the iSE is composed of a bilayer of metals Cr/Au (Cr used as an adhesion layer for Au—could also use other adhesion layers, e.g. Ti, Titanium), at approximately 25 Å and 800 Å, respectively, and is located approximately 5-20 µm from the contact electrodes and is approximately 5 µm wide. Alternatively, the iSE could be a single layer metal that does no require a binder layer. FIG. 2(b) is an actual view of the electrodeposition set-up. In operation, a drop of electrolyte PBS is applied to the device, and a positive voltage $V_d$ is applied to the sacrificial electrode, with both contact electrodes grounded. Au atoms from the sacrificial electrode are oxidized by the positive potential and dissolve in the PBS as Au ions, and are reduced at the grounded electrode/CNT and redeposit as metal atoms. Here the applied voltage is reduced to avoid electrolysis of water, and finer adjustments will be made later to control the size and density of Au nanoparticles.

By way of example, referring to FIGS. 3(a)-(d), the high sensitivity of particle density and size in accordance with changes in applied voltage is illustrated. The SEM images show a series of carbon nanotubes decorated with Au nanoparticles. With the deposition time held constant at 2 minutes, by slightly increasing the deposition voltage $V_d$, the number of nanoparticles increases substantially, and the size of the nanoparticles also shows an increasing trend, from 20 nm to as large as 300 nm. Note that at all voltages, the sizes of the nanoparticles are not homogenous, and the variation of particle size increases with deposition voltage. At 1.3V, for this specific device, there is only one nanoparticle deposited on the nanotube, and the size of the nanoparticle is about 60 nm (FIG. 3(a)). This is of special interest for sensor applications because it makes single molecule sensitivity possible by minimizing possible defects and noise caused by the nanoparticles. At 1.32V, there are 4 nanoparticles, and the sizes are 170 nm, 160 nm, 100 nm, 110 nm, respectively (FIG. 3(b)). At 1.34V, there are 7 nanoparticles, and the diameters are 67 nm, 324 nm, 337 nm, 212 nm, 246 nm, 201 nm and 33 nm, respectively (FIG. 3(c)). At the highest voltage 1.36V, there are over 30 nanoparticles on the nanotube, and the size ranges from 27 nm to over 300 nm (FIG. 3(d)). In the middle, there are over 10 nanoparticles with diameters less than 100 nm, and on the two sides, nanoparticles are typically much larger, with diameters of hundreds of nanometers.

In alternative embodiments, other materials may be used as the deposit material, such as Ag. Appropriate changes to the deposition set up are implemented to account of use of other deposit materials.

Figure 4:
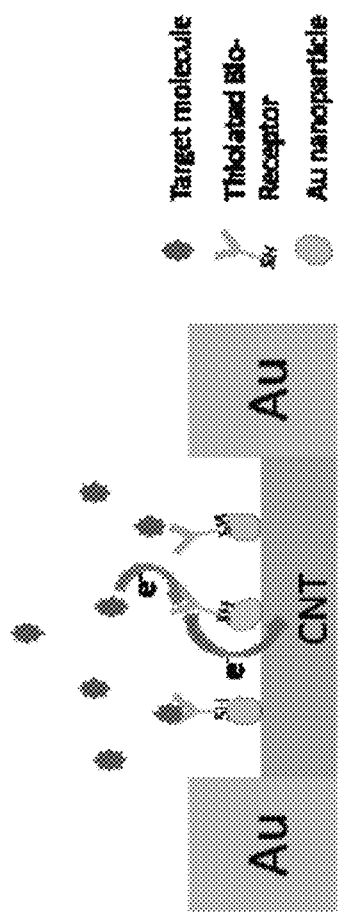
FIG. 4 illustrates is a schematic showing anchoring of receptors to nanoparticles deposited on a carbon nanotube.

Once decorated with appropriate nanoparticles, select receptors can be anchored to the nanoparticles in order to prepare the CNTFET for use as a sensor. This is shown schematically in FIG. 4. Certain metals have strong affinity to specific chemical groups, and the affinity can be utilized to realize effective surface modifications. For example, gold atoms are known to interact strongly with sulfur atoms in thiols and form a strong covalent bond. In the present embodiment, the Au nanoparticles are deposited on the CNT sidewalls as anchoring sites to immobilize thiol-terminated biomolecules to the nanotube for sensor applications. The strong covalent bond between the gold and thiol provides for a more robust bond compared to nonspecific adsorption of biomolecules onto the CNT sidewalls. In addition, the catalytic nature and suitability for binding to the thiol as well as the excellent conductivity of the metallic Au nanoparticles makes the delivery of the chemical event at the biomolecule to the CNT channel much easier.

Figure 5:
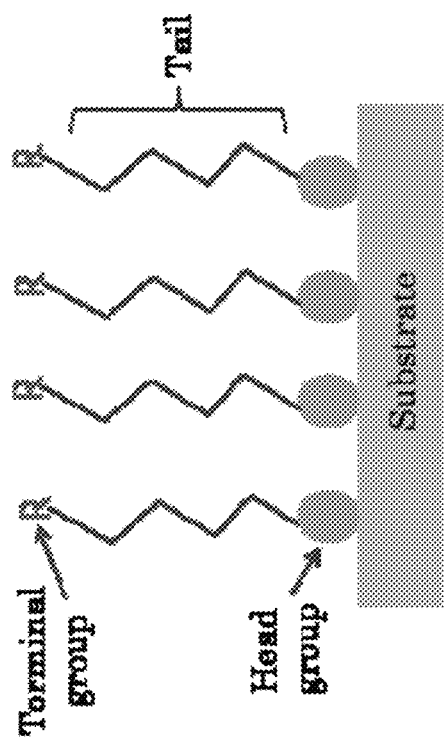
FIG. 5 illustrates a schematic of a CNTFET which has been passivated using a self assembled monolayer (SAM) to avoid non-specific binding of bioreceptors.

In order to better control binding of the bioreceptors to the Au nanoparticles in particular and avoid non-specific binding to, for example, the $SiO_2$ surface, a self assembled monolayer (SAM) may be used. An SAM is an organized layer of molecules which consists of a head and a tail, with the head showing a specific affinity for a substrate, and the tail having a desired functional group at the terminal. SAMs have been widely used for surface property modifications in electronic devices, especially microelectrochemical systems (MEMS) and nanoelectromechanical systems (NEMS). Its working mechanism is shown in FIG. 5. The original substrate has an affinity for head group of the SAM, and after modification, the substrate has the property of the terminal functional group R. The use of an SAM provides for an effective method to combine the desirable properties of the substrate such as electrical conductivity, mechanical robustness, to the SAM molecule's chemical properties.

In order to passivate the $SiO_2$ surface for nonspecific protein adsorption, two properties are desired for the SAM molecules. First, the head group should have a strong affinity to $SiO_2$ surface. Second, the tail should have good protein resistivity. Polyethylene glycol (PEG) SAMs including methoxy-terminated PEG 2000 have been shown to have good protein resistivity. To realize strong affinity to $SiO_2$, the silane functional group having the following molecular structure is added to one end of the molecule:

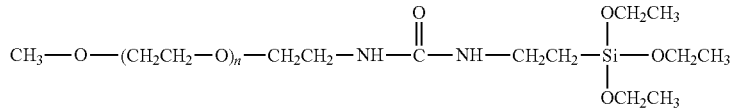

Figure 6:
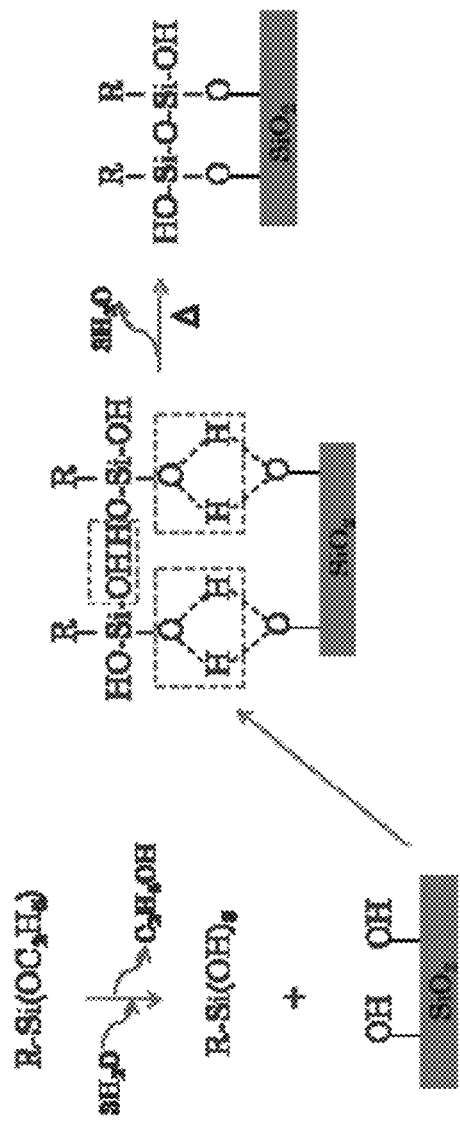
FIG. 6 illustrates intermolecular linking of SAM molecules.

In the presence of water molecules, the silane functional groups of the PEG hydrolyze and form trisilanols. The trisilanols interact with the $SiO_2$ and hydrogen bond with the surface bound water molecules. With mild heating, the water molecule is lost and a covalent siloxane bond is formed. When the distance and orientation between the groups become favorable, the tri-silanol head groups can interact with each other and intermolecular crosslinking takes place as shown in FIG. 6. This passivation treatment helps to reduce any non-specific binding of the bioreceptors.

In a particular application of the devices and processes described herein, the electrodeposited Au nanoparticles serve as specific binding sites for thiol-terminated glucose oxidase, and the presence of glucose can be detected using the redox reaction between glucose and glucose oxidase. The particular electrical configurations and processes for sensing reactions within the CNTFETs are well known to those skilled in the art. By way of example the teachings of A. Star et al. (cited above) and K. J. Cash, H. A Clark, Trends in Molecular Medicine, Volume 16, Issue 12, 584-593, 23 Sep. 2010 are hereby incorporate by reference in their entirety. The glucose oxidase is functionalized with one or multiple thiols to covalently bind to the Au nanoparticles. The thiolated GOx is selectively deposited to the Au nanoparticles of the carbon nanotube FET, using the above mentioned SAM passivation method. Fluorescent labels might also be used on the protein to confirm the successful attachment using confocal fluorescent imaging techniques. After the device is fully functionalized, sensing tests can be taken. For glucose sensing, the device is placed in an aqueous environment. A PBS buffer is applied to the nanotube device, and the device conductance is monitored in real time with a constant gate. Then various concentrations of glucose solution are added into the buffer using a pipette, and the change in conductance is recorded. The applied gate voltage will be tested to find the most pronounced signal, and different concentrations will be added to measure the sensitivity of the device. Once nanotube device parameters are optimized for sensing glucose, the optimized devices may be used as the sensor portion of the transdermal devices described herein.

Figure 7:
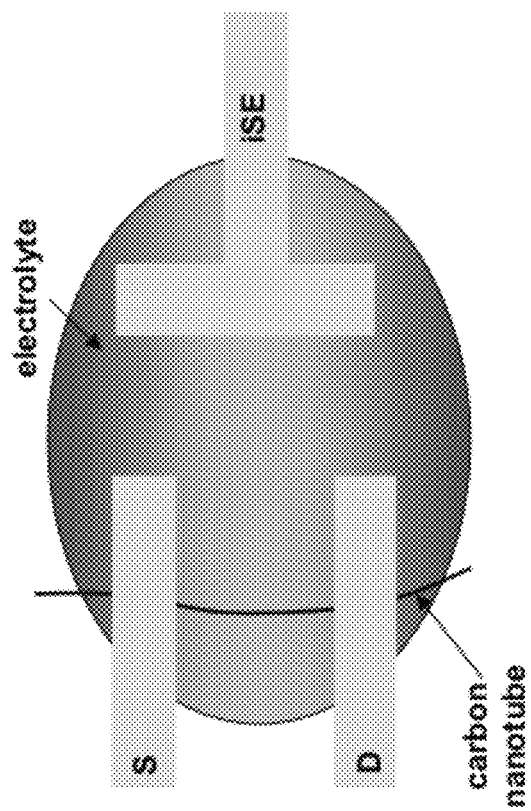
FIG. 7 illustrates an alternative arrangement of the CNT and iSE.

In an alternative embodiment to those described above, the CNTFET is decorated with metallic (e.g., Au) nanoparticles that are pre-bound with selected bioreceptor molecules (e.g., thiolated GOx). The iSE configuration can have different shapes, as seen in FIG. 7, e.g., the rectangular iSE could run parallel to the CNT, and shape of the iSE. Further still, bioreceptors could be pre-bound to the iSE prior to application of the external electric field, such that the metallic nanoparticles already include the bioreceptors at the time of decoration of the CNT. A masking layer is used over the electrodes, e.g. polymethylmethacrylate (PMMA) or the negative-tone photoresist known as SU-8 to protect the contact electrodes from decoration. The protection layer would form a physical barrier to the decorating species. Such materials are described in J. Zhang, A. Boyd, A. Tselev, M. Paranjape, and P. Barbara, *Mechanism of $NO_2$ Detection in Carbon Nanotube Field Effect Transistor Chemical Sensors*, Appl. Phys. Lett. 88(12), 2006 which is incorporated herein by reference in its entirety.

By way of non-limiting example, the decorated CNTFETs are used in place of the photonic-based and other sensors described previously. More particularly, referring, for example, to FIG. 2 of U.S. Pat. No. 6,887,202, a decorated CNTFET would be in the position of detection layer 203 such that it is exposed to the sample from capillary 202. Using the Au decorated CNTFET with thiol-terminated glucose oxidase bioreceptors bound thereto, glucose present in the sample would react with the bioreceptors and cause a measurable electrical response.

Additional descriptive material that may be helpful to understanding the present embodiments is found in "Fabrication and Functionalization of Carbon Nanotube Field Effect Transistors for Bio-Sensing Applications" by Jianyun Zhou, dated Dec. 17, 2009, submitted to the faculty of the Graduate School of Arts and Sciences of Georgetown University and incorporated herein by reference in its entirety.

It should be apparent to one of ordinary skill in the art that other embodiments can be readily contemplated in view of the teachings of the present specification. Such other embodiments, while not specifically disclosed nonetheless fall within the scope and spirit of the present invention. Thus, the present invention should not be construed as being limited to the specific embodiments described above, and is solely defined by the following claims.

The invention claimed is:

1. A process for forming a functionalized sensor for sensing a molecule of interest comprising:
    providing at least one carbon nanotube having a first and a second electrode in contact therewith on a substrate;
    providing a third, sacrificial electrode, including a decorating material, on the substrate, a predetermined distance from the at least one carbon nanotube having a first and a second electrode in contact therewith, wherein the decorating material has a bonding affinity for bioreceptors that react with the molecule of interest; and
    applying a voltage to the third, sacrificial electrode, causing the decorating material to form nanoparticles of the decorating material on the at least one carbon nanotube via electrodeposition.

2. The process according to claim 1, wherein the third, sacrificial electrode is formed of a bilayer of Cr and Au.

3. The process according to claim 2, wherein the decorating material is Au.

4. The process of claim 2, wherein the bilayer of Cr and Au comprises an
    approximately 25 Å Cr layer and an approximately 800 Å Au layer and is approximately 5 µm wide.

5. The process according to claim 1, wherein the predetermined distance is approximately 5-20 µm from the first and second electrodes.

6. The process according to claim 1, wherein a size and density of the nanoparticles is related to the applied voltage.

7. The process according to claim 1, further comprising passivating the substrate to reduce adsorption of the bioreceptors.

8. The process according to claim 7, wherein passivating includes introducing a self assembled monolayer (SAM) of molecules to the substrate, wherein said molecules the SAM include a head group with an affinity for the substrate and a tail having protein resistivity.

9. The process of claim 8, wherein the substrate is $SiO_2$ and said molecules comprise a methoxy-terminated polyethylene glycol (PEG).

10. The process of claim 1, further comprising binding the bioreceptors to the nanoparticles.

11. The process of claim 1, wherein the bioreceptors are thiol-terminated glucose oxidase and the molecule of interest is glucose.

12. The process of claim 1, wherein the at least one carbon nanotube is selected from the group consisting of single-wall carbon nanotubes and multi-wall carbon nanotubes.

13. The process according to claim 1, wherein the third, sacrificial electrode is formed of a bilayer of Ti and Au.

14. The process according to claim 1, wherein the at least one carbon nanotube is a network of carbon nanotubes.

15. The process according to claim 14, wherein the network of carbon nanotubes includes carbon nanotubes selected from the group consisting of single-wall carbon nanotubes and multi-wall carbon nanotubes.

* * * * *

UNITED STATES PATENT AND TRADEMARK OFFICE
CERTIFICATE OF CORRECTION

| | |
|---|---|
| PATENT NO. | : 9,302,908 B2 |
| APPLICATION NO. | : 12/970997 |
| DATED | : April 5, 2016 |
| INVENTOR(S) | : Makarand Paranjape et al. |

It is certified that error appears in the above-identified patent and that said Letters Patent is hereby corrected as shown below:

IN THE CLAIMS:

In column 6, lines 6 and 7 (within claim 1), please change "providing a third, sacrificial electrode, including a decorating material, on the substrate, a predetermined distance" to -- providing a third electrode, including a decorating material on the substrate a predetermined distance --

In column 6, line 12 (within claim 1), please change "applying a voltage to the third, sacrificial electrode, caus-" to -- applying a voltage to the third electrode, caus- --

In column 6, lines 14 and 15 (within claim 1), please change "decorating material on the at least one carbon nanotube via electrodeposition." to -- decorating material on the at least one carbon nanotube. --

In column 6, lines 16 and 17 (within claim 2), please change "The process according to claim 1, wherein the third, sacrificial electrode is formed of a bilayer of Cr and Au." to -- The process according to claim 1, wherein the third electrode is formed of a bilayer of Cr and Au. --

In column 6, lines 20-23 (within claim 4), please change "The process of claim 2, wherein the bilayer of Cr and Au comprises an approximately 25 Å Cr layer and an approximately 800 Å Au layer and is approximately 5 µm wide." to -- The process of claim 2, wherein the Cr is approximately 25 Å and the Au is approximately 800 Å and is approximately 5 µm wide. --

In column 6, lines 33-35 (within claim 8), please change "includes introducing a self assembled monolayer (SAM) of molecules to the substrate, wherein said molecules the SAM include a head group with an affinity for the substrate and a" to -- includes introducing a self-assembled monolayer (SAM) to the substrate, wherein the SAM includes head group with an affinity for the substrate and a --

Signed and Sealed this
Seventh Day of June, 2016

Michelle K. Lee
*Director of the United States Patent and Trademark Office*

CERTIFICATE OF CORRECTION (continued)
U.S. Pat. No. 9,302,908 B2

In column 6, line 38 (within claim 9), please change "said molecules comprise a methoxy-terminated polyethylene" to -- the SAM is a methoxy-terminated polyethylene --

In column 6, lines 48 and 49 (within claim 13), please change "The process according to claim 1, wherein the third, sacrificial electrode is formed of a bilayer of Ti and Au." to -- The process according to claim 1, wherein the third electrode is formed of a bilayer of Ti and Au. --